United States Patent [19] [11] 4,393,044
Takada et al. [45] Jul. 12, 1983

[54] STEROID ESTER, AND COSMETICS AND OINTMENTS CONTAINING THE SAME

[75] Inventors: Atsunobu Takada, Yokohama; Yuzo Higaki, Machida, both of Japan

[73] Assignee: The Nisshin Oil Mills Limited, Tokyo, Japan

[21] Appl. No.: 265,847

[22] Filed: May 21, 1981

[30] Foreign Application Priority Data

May 29, 1980 [JP] Japan ................................. 55/71708
Jun. 10, 1980 [JP] Japan ................................. 55-78156

[51] Int. Cl.³ .................... A61K 7/42; A61K 7/02; A61K 7/025
[52] U.S. Cl. ..................................... 424/59; 424/63; 424/64; 424/DIG. 5; 424/238; 260/397.2
[58] Field of Search .................... 260/397.2; 424/238, 424/63, 64, 59

[56] References Cited
U.S. PATENT DOCUMENTS
4,309,448 1/1982 Takaishi et al. .................. 260/397.2

OTHER PUBLICATIONS
Gibson et al., "Journal of Physical Chemistry" vol. 77, No. 6 (1973) pp. 837-845.

Cataline et al., "Journal of the American Pharm. Ass." (1944) pp. 107-108.
Fieser et al., "Steroids" (1959) Reinhold Publishing Co. pp. 364-365.

Primary Examiner—Elbert L. Roberts
Attorney, Agent, or Firm—Bacon & Thomas

[57] ABSTRACT

Steroid ester is formed by the reaction between a carboxylic component and cholesterol or methylsterol having two methyl groups attached to the 4-position of the sterol skeleton. The carboxylic component is an α-branched carboxylic acid having a general formula:

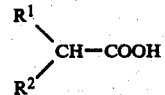

(where $R^1$ is an alkyl group having at least two carbon atoms, and $R^2$ is an alkyl group having at least four carbon atoms) or a reactive derivative of said α-branched carboxylic acid. The steroid ester is high in resistance to hydrolysis, exhibits an excellent water-embracing property and, thus, provides an effective oil phase material or base material of cosmetics or ointments.

51 Claims, No Drawings

STEROID ESTER, AND COSMETICS AND OINTMENTS CONTAINING THE SAME

BACKGROUND OF THE INVENTION (1) Field of the Invention:

This invention relates to a novel steroid ester as well as cosmetics and ointments containing the same, and more particularly to an ester between a certain kind of steroid and an α-branched carboxylic acid as well as cosmetics and ointments containing the same.

(2) Description of the Prior Art:

Esters such as steroid esters are widely used as an oil phase material or base material of cosmetics for the skin or hair, or of ointments. For example, stearic acid ester or oleic acid ester of cholesterol is contained in stick-like cosmetics such as lipstick, eyeshadow and stick pomade as well as in cosmetic cream, ointment, etc. These linear fatty acid esters of cholesterol are excellent in water-embracing or -encapsulating property and emulsifying property, exhibit affinity with the skin, and are not irritative. These properties render the esters desirable for use as an oil phase material or additive of, for example, cosmetics or ointments. However, these esters are undesirably solidified at temperatures near the human skin temperature. For example, cholesteryl stearate has a melting point of 75° to 85° C., with cholesteryl oleate having a melting point of 40° to 45° C., with the result that the cosmetics containing these esters give uncomfortable feel to the user when applied to the skin. It should also be noted that these esters are decomposed into cholesterol and fatty acids under the action of lipase present on the skin.

Japanese Patent Disclosure (Kokai) No. 52-79030 teaches the idea of mixing into cosmetics esters of fatty acids such as stearic acid and oleic acid with phytosterol, which resembles cholesterol in chemical structure, or its hydrogenated derivative. The above-noted prior art certainly teaches that the particular ester is not irritative to the skin and can be used comfortably, but does not teach at all the properties of the ester such as water-embracing property, emulsifying property, water-holding property and resistance to hydrolysis.

The present inventors have examined the resistance to hydrolysis of cholesteryl stearate, cholesteryl oleate, phytosteryl stearate and phytosteryl oleate under the ordinary hydrolyzing (or saponifying) conditions of oil and fat. Specifically, these esters were heated at 80° to 85° C. within a ½ N alcoholic KOH solution, with the result that any of these esters was completely hydrolyzed within 1 hour of heating. To be brief, the conventional linear fatty acid esters of steroid are unsatisfactory in resistance to hydrolysis.

It is further required that an oil phase material contained in, for example, cosmetics be high in water-embracing property. "Water-embracing property" means the capability of embracing and holding water in an oil phase material. An oil phase material high in water-embracing property permits decreasing the amount of surfactant contained in the cosmetics and enables water to be retained on the skin surface, giving the user a moist feel. Lanolin certainly exhibits a high water-embracing property, but produces allergy effect. Thus, it is a matter of serious concern in this field to develop an oil phase material of cosmetics which can be used in place of lanolin. Japanese Patent Disclosure (Kokai) No. 52-95700 teaches the idea of removing the allergy component from lanolin, but the resultant material leaves room for further improvement. A linear fatty acid ester of cholesterol is also known to exhibit a high water-embracing property, but fails to provide a satisfactory oil phase material of cosmetics.

SUMMARY OF THE INVENTION

An object of this invention is to provide a steroid ester suitable for use as an oil phase material of cosmetics and ointments.

Another object is to provide a steroid ester excellent in resistance to hydrolysis.

Another object is to provide a steroid ester which does not irritate the human skin.

Still another object of this invention is to provide cosmetics and ointments containing such steroid ester.

These and other objects which will be apparent from the following detailed description are achieved by a steroid ester obtained by reacting at least one steroid component selected from the group consisting of cholesterol and methylsterols having two methyl groups attached to the 4-position of the sterol skeleton with at least one carboxylic acid-based component selected from the group consisting of α-branched carboxylic acids having a general formula:

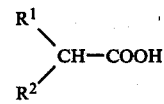

(where $R^1$ is an alkyl group having at least two carbon atoms and $R^2$ is an alkyl group having at least four carbon atoms), and reactive derivatives of said α-branched carboxylic acid.

The cosmetics and ointments containing such steroid ester also fall within the scope of this invention.

DETAILED DESCRIPTION OF THE PREFERRED EMBODIMENTS

The steroid component used for producing the steroid ester of this invention is selected from the group consisting of cholesterol, methylsterols having two methyl groups attached to the 4-position of the sterol skeleton, and mixtures thereof. As is known well in the art, "steroid" is a general term of the derivatives and analogs of sterol, i.e., perhydro-1,2-cyclopentanophenanthrene compound having hydroxyl group attached to the 3-position, methyl groups attached to the 10- and 13-positions and a side chain group attached to the 17-position. In other words, steroid represents the compounds having the following skeletal structure:

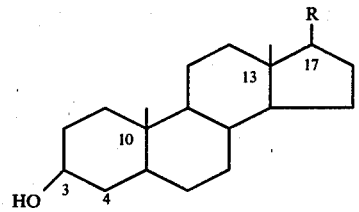

where R is a side chain group.

The methyl sterols used in this invention represent a steroid having two methyl groups attached to the 4-position of the skeletal structure shown above and include, for example, trimethylsteroid such as dihydrolanosterol, lanosterol, dihydroagnosterol, agnosterol, cycloartanol, cycloartenol, 2,4-methylenecycloartanol, cyclolaudenol and cyclobranol. A mixture of these methylsterols can also be used in this invention. A typical mixture, which is commercially available, is isocholesterol, i.e., mixture of dihydrolanosterol, lanosterol, dihydroagnosterol, agnosterol, etc., obtained by decomposing wool fat.

A mixture of cholesterol and methylsterol can also be used in this invention as the steroid component. Incidentally, methylsterol is preferred to cholesterol in terms of the resistance to hydrolysis of the resultant ester.

The carboxylic acid-based component which can produce the steroid ester of the invention by the reaction with the above steroid component includes α-branched carboxylic acids having a general formula:

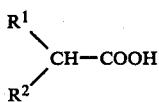
(I)

reactive derivatives of said carboxylic acids, and a mixture thereof. In formula (I), $R^1$ represents an alkyl group having at least two carbon atoms and $R^2$ denotes an alkyl group having at least four carbon atoms. In general, the sum of the carbon atoms contained in $R^1$ and $R^2$ is up to 24. The α-branched carboxylic acids mentioned include, for example, 2-ethylhexanoic acid, 2-hexylundecanoic acid (available as isopalmitic acid from Nissan Chemical Co., Ltd., Japan), 2-heptylundecanoic acid (available as Diadole 18GA from Mitsubishi Chemical Co., Ltd., Japan), a carboxylic acid having the following chemical structure:

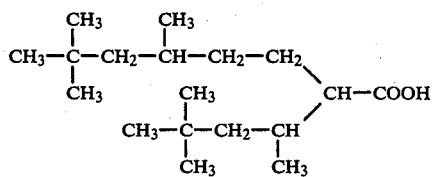

(available as Fineoxocol 180 acid from Nissan Chemical), 2-decyltetradecaonic acid, 2-undecyltetradecanoic acid, 2-decylpentadecanoic acid, and 2-undecylpentadecanoic acid. It is also possible to use a mixture of these α-branched carboxylic acids, including, for example, Hisocol 246 acid i.e., mixture of 2-decyltetradecanoic acid, 2-undecyltetradecanoic acid, 2-decylpentadecanoic acid and 2-undecylpentadecanoic acid, obtained by oxidizing "Hisocol 246" (trademark of an alcohol mixture produced by Ito Seiyu K.K.).

The term "reactive derivatives" of the α-branched carboxylic acids described above is intended to mean those derivatives which are capable of performing reactions with the steroid component to produce steroid esters of the invention. The reactive derivatives mentioned include, for example, acid halides, particularly acid chlorides, and acid anhydrides. These derivatives, particularly, acid chlorides, are superior to the free α-branched carboxylic acids in reactivity. As is known well in the art, a free carboxylic acid can be readily converted into its corresponding acid chloride by reacting the free carboxylic acid with a chlorinating agent such as phosphorus trichloride, phosphorus pentachloride or thionyl chloride.

The carboxylic acid-based component reacts with the hydroxyl group attached to the 3-position of the steroid so as to form the desired steroid ester of the present invention. Basically, the reaction between the steroid component and the carboxylic acid-based component proceeds in accordance with the esterification process well known in the art. In general, these two reactants are reacted at such temperature for such period of time sufficient to permit producing the desired ester. Where, a free carboxylic acid is used as the carboxylic acid-based component, the esterification reaction is carried out under somewhat severe conditions. Specifically, the esterification reaction is carried out at about 150° C. to about 270° C., preferably, at about 180° C. to about 240° C. for about 7 hours to about 35 hours in the presence of the ordinary esterification catalyst such as hydrogen chloride, sulfuric acid, boron trifluoride, p-toluenesulfonic acid or tin chloride. The reaction between carboxylic acid and steroid can be carried out under a molar ratio of 1:1, but the reaction is facilitated if either of the two reactants is used in excess (in general, carboxylic acid is used in excess). To be more specific, the molar ratio of carboxylic acid to steroid is about 1.5:1.0 to about 1.0:1.5 preferably about 1.1:1.0 to about 1.0:1.1. It is convenient to carry out the esterification reaction within and under reflux of an inert organic solvent such as benzene or xylene.

If a reactive derivative, particularly, an acid chloride, is used as the carboxylic acid-based component, the esterification reaction proceeds more easily. To be more specific, the desired ester can be obtained by simply reacting the acid chloride with the steroid at about 50° C. to 200° C., preferably about 80° C. to 150° C. for about 5 hours to 15 hours in the absence of a catalyst. It suffices to set the molar ratio of acid chloride to steroid at 1:1, though different ratios, e.g., 1.0:1.1 to 1.1:1.0, may also be employed. It is convenient to carry out the esterification reaction under a reduced pressure, e.g. 1 mmHg to 100 mmHg. Where the acid chloride is solid, the esterification reaction is facilitated if carried out within the organic solvent mentioned above.

The resultant steroid ester of the present invention is excellent in resistance to hydrolysis and is superior to the conventional ester in the water-embracing property. Also, the ester of the present invention does not irritate the human skin, is almost in a liquid form under room temperature, and is highly compatible and miscible with other components. It follows that the steroid ester of the present invention is useful as an oil phase material, base material or additive of various cosmetics or ointments. When used as, particularly, an oil phase material of cosmetics, the ester permits readily forming a stable emulsion. Also, when applied to the human skin, the ester serves to form a uniform protective film.

The following Examples are given to illustrate the production of steroid esters of the invention.

EXAMPLE 1

A solution prepared by dissolving 28.7 g (0.10 mole) of 2-heptylundecanoic acid in 100 g of benzene was heated to 60° C. and 5 g of phosphorus trichloride was slowly added dropwise into the solution which was kept stirred. Then, the reaction between the acid and the chloride was carried out for 5 hours under reflux of benzene, followed by cooling the reaction system and removing the lower phosphorus oxychloride layer from the reaction system. Further, benzene was removed from the upper benzene layer by means of distillation so as to obtain 30 g of the corresponding acid chloride. The acid chloride, 30 g, and cholesterol, 38.6 g (0.10 mole), were put in a flask and an esterification reaction was carried out as above between cholesterol and stearic acid (Control 1), isostearic acid produced by Emery Inc. (Control 2), or oleic acid (Control 3). The properties of the resultant cholesterol esters are also shown in Table 1.

TABLE 1

| | Acid | Produced Ester | | | | | |
|---|---|---|---|---|---|---|---|
| | | Appearance | Odor | Melting point (°C.) | Acid value | Saponification value | Hydroxyl value |
| Example 3 | 2-ethylhexanoic acid | slightly yellowish brown (solid) | None | 34 | 0.03 | 105.5 (110.0) | 0.6 |
| Example 4 | 2-hexyldecanoic acid | slightly yellowish and viscous (liquid) | None | — | 0.1 | 85.0 (90.0) | 1.2 |
| Example 5 | 2-heptylundecanoic acid | slightly yellowish and viscous (liquid) | None | — | 0.2 | 82.5 (85.8) | 1.0 |
| Example 6 | Fineoxocol 180 acid | slightly yellowish and viscous (liquid) | None | — | 0.2 | 78.8 (85.8) | 1.0 |
| Example 7 | Hisocol 246 acid | slightly yellowish and viscous (liquid) | None | — | 0.5 | 71.0 (74.0) | 0.8 |
| Control 1 | stearic acid | brown (solid) | None | 77 | 0.2 | 86.6 (86.5) | 1.6 |
| Control 2 | isostearic acid | slightly yellow (solid) | None | 37 | 0.05 | 85.2 (85.2) | 1.1 |
| Control 3 | Oleic acid | yellow (solid) | None | 42 | 0.3 | 86.1 (86.0) | 1.2 |

*For determining the saponification value, 3.0 ± 0.5 g of the sample was added to 20 ml of 1N n-propyl alcohol solution of KOH and the saponification was carried out for 3 hours at 140 to 150° C. under reflux condition. The numeral put in the parenthesis represents the calculation value.

was carried out for 4 hours at 100° to 110° C. under a reduced pressure (20 mmHg). Then, the reaction mixture was dissolved in benzene and the esterified product was extracted so as to obtain 60 g of a desired yellow liquid ester.

EXAMPLE 2

A flask was charged with 57.4 g (0.20 mole) of 2-heptylundecanoic acid, 38.6 g (0.10 mole) of cholesterol and 0.48 g of p-toluenesulfonic acid, and an esterification reaction was performed for 20 hours under reflux of xylene. After the reaction, the excess 2-heptylundecanoic acid was removed by means of vacuum distillation at 200° to 250° C. so as to obtain 64 g of a desired slightly brownish liquid ester.

EXAMPLES 3 to 7

An esterification reaction was carried out for about 25 hours at 200° to 220° C. between 0.11 mole of each of the α-branched carboxylic acids shown in Table 1 and 0.10 mole of cholesterol in the presence of tin chloride acting as a catalyst. After the reaction, the catalyst was removed by filtration, followed by removing the excess acid and traces of cholesterol at 200° to 250° C. under a reduced pressure so as to obtain desired slightly yellowish esters in an amount substantially equal to the theoretical value, i.e., desired esters of cholesteryl-2-ethylhexanoate (Example 3), cholesteryl-2-hexydecanoate (Example 4), cholesteryl-2-heptylundecanoate (Example 5), ester between cholesterol and Fineoxocol 180 acid (Example 6), and ester between cholesterol and Hisocol 246 acid (Example 7). Table 1 also shows the properties of these cholesterol esters. Further, Table 1 covers Controls 1 to 3 in which an esterification reac- The cholesterol esters shown in Table 1 were tested for the resistance to hydrolysis under different hydrolyzing conditions with respect to the reagent, temperature and time, with the results as shown in Table 2.

TABLE 2

| | Hydrolyzing Condition Rate of Hydrolysis (%) | | | | | | | |
|---|---|---|---|---|---|---|---|---|
| | ½N alcoholic coustic potash (25 ml) 85° C. | | 1N alcoholic coustic potash (20 ml) 85° C. | | | 1N n-propyl-alcohol solution of KOH (20 ml) 140 ~ 150° C. | | |
| Esters | 2 hrs. | 3 hrs. | 1 hr. | 2 hrs. | 3 hrs. | 1 hr. | 2 hrs. | 3 hrs. |
| Example 3 | 16 | 19 | — | — | 36 | 66 | 94 | 96 |
| Example 4 | 15 | 18 | — | — | 34 | 65 | 92 | 94 |
| Example 5 | 15 | 18 | — | — | 36 | 65 | 93 | 96 |
| Example 6 | 10 | 15 | — | — | 30 | 61 | 90 | 92 |
| Example 7 | 15 | 17 | — | — | 33 | 64 | 93 | 96 |
| Control 1 | 100 | 100 | 100 | 100 | 100 | 100 | 100 | 100 |
| Control 2 | 100 | 100 | 100 | 100 | 100 | 100 | 100 | 100 |
| Control 3 | 100 | 100 | 100 | 100 | 100 | 100 | 100 | 100 |

Table 2 shows that any of the conventional esters, i.e., stearic acid ester, oleic acid ester and isostearic acid ester, is completely hydrolyzed (100% of hydrolysis) by ½ N alcoholic caustic potash within 2 hours in contrast to less than 20% of hydrolysis even 3 hours later for the esters of the present invention. In other words, the ester of the present invention is excellent in resistance to hydrolysis.

The esters shown in Table 2 were further tested for the water-embracing property, with the results as shown in Table 3.

TABLE 3

| Product Ester | Water-Embracing Property* | | | |
|---|---|---|---|---|
| | Ester itself | Ester Addition to Vaseline | | |
| | | 2% | 4% | 6% |
| Example 3 | 200 g | 105 g | 110 g | 110 g |
| Example 4 | 215 g | 110 g | 120 g | 120 g |
| Example 5 | 220 g | 115 g | 115 g | 90 g |
| Example 6 | 280 g | 140 g | 150 g | 120 g |
| Example 7 | 230 g | 120 g | 125 g | 125 g |
| Control 1 | 105 g | 42 g | 76 g | 62 g |
| Control 2 | 120 g | 55 g | 80 g | 70 g |
| Control 3 | 110 g | 51 g | 60 g | 46 g |
| Lanolin | 60 g | 15 g | 30 g | 25 g |

*Ion exchanged water was added to 100 g of the sample while fully stirring the system so as to prepare a w/o type emulsion. The water-embracing property was determined by measuring the maximum amount of the ion exchanged water added which permits maintaining the w/o type emulsion.

Table 3 shows that the esters of the present invention (Examples 3 to 7) exhibit a water-embracing property more than 3 times as high as that of lanolin and are markedly superior to the conventional esters (Controls 1 to 3) in water-embracing property.

The esters of the present invention (Examples 3 to 7) were tested for the irritativeness to the human skin. Specifically, a closed patch test was performed as follows: A lint cloth on inch square was coated with the ester sample and attached to the skin area of a healthy person on the flexion side of the upper arm from which the horny layer and sebum have been removed. The lint cloth thus attached to the skin area was covered with an oilpaper and the oilpaper was fixed to the skin at four corners by a sticking plaster, followed by bandaging the ester-applied portion. This condition was maintained for 24 hours, 48 hours and 72 hours. This test was applied to 20 healthy persons. Irritativeness was not recognized at all in any of Examples 3 to 7.

EXAMPLE 8

A solution prepared by dissolving 28.7 g (0.10 mole) of Diadole 18GA in 100 g of benzene was heated to 60° C. and 5 g of phosphorus trichloride was slowly added dropwise into the solution while stirring the solution, followed by carrying out the reaction for 5 hours under reflux of benzene. Then, the reaction mixture was cooled and the lower layer of phosphorus oxychloride was removed from the reaction mixture. Further, benzene was removed from the upper benzene layer by means of distillation so as to obtain 30 g of the corresponding acid chloride. An esterification reaction was carried out for 8 hours at 100° to 110° C. under a reduced pressure between 30 g of the acid chloride and 33.7 g (0.10 mole) of isocholesterol (produced by Yoshikawa Seiyu K.K., said isocholesterol having a melting point of 142.2° to 143.5° C., an acid value of 0.35 and a hydroxyl value of 166.3). The reaction mixture was dissolved in benzene to extract the esterified product, followed by removing benzene from the extract so as to obtain 50.0 g of the desired ester of yellowish brown transparent liquid form. The product ester was found to exhibit a hydroxyl value of 5.3.

EXAMPLE 9

An esterification reaction was carried out at 200° to 220° C. under reflux of xylene between 43.3 g (0.30 mole) of 2-ethylhexanoic acid and 33.7 g (0.10 mole) of isocholesterol in the presence of 0.23 g, which is 0.3% of the reactants, of p-toluenesulfonic acid acting as the esterification catalyst. The reaction was continued until water was generated in an amount substantially equal to the calculation value. After the reaction, xylene was removed from the reaction mixture, followed by further removing the unreacted 2-ethylhexanoic acid at 180° to 200° C. under a reduced pressure so as to obtain 45.0 g of the desired ester of yellowish brown transparent liquid form. The product ester was found to exhibit an acid value of 0.1 and an hydroxyl value of 4.6.

EXAMPLE 10

An esterification reaction was carried out at 200° to 220° C. under reflux of xylene between 76.8 g (0.30 mole) of "Isopalmitic Acid" (trademark of 2-hexyldecanoic acid produced by Nissan Chemical Co., Ltd.) and 33.7 g (0.10 mole) of isocholesterol in the presence of 0.22 g, which is 0.2% of the reactants, of tin chloride acting as the catalyst. The reaction was continued until water was generated in an amount substantially equal to the calculation value. After the reaction, xylene was removed from the reaction mixture, followed by decoloring the remaining reaction mixture with china clay. Further, the decolored mixture was filtered and, then, subjected to a vacuum distillation at 200° to 250° C. so as to remove the unreacted 2-hexyldecanoic acid and, thus, to obtain 47.6 g of the desired ester. The product ester was found to exhibit an acid value of 0.1 and a hydroxyl value of 0.6.

EXAMPLE 11

An esterification reaction was carried out at 200° to 220° C. under reflux of xylene between 87.0 g (0.30 mole) of "Fineoxocol 180 acid" (trademark of Nissan Chemical Co., Ltd.) and 33.7 g (0.10 mole) of isocholesterol in the presence of 0.36 g, which is 0.3% of the reactants of tin chloride. The reaction was continued until water was generated in an amount sustantially equal to the calculation value. After the reaction, xylene was removed from the reaction mixture, followed by decoloring the remaining reaction mixture with china clay. Further, the decolored mixture was filtered and, then, subjected to a vacuum distillation at 200° to 250° C. so as to remove the unreacted Fineoxocol 180 acid and, thus, to obtain 52.5 g of the desired ester. The product ester was found to exhibit an acid value of 0.0 and a hydroxyl value of 0.44.

EXAMPLE 12

An esterification reaction was carried out as in Example 11 between 0.3 mole of Hisocol 246 acid prepared by oxidizing "Hisocol 246" (trademark of Ito Seiyu K.K.) and 0.1 mole of isocholesterol in the presence of tin chloride catalyst so as to obtain 55.7 g of the desired ester. The product ester was found to exhibit an acid value of 0.1 and a hydroxyl value of 0.8.

The esters produced in Examples 8 to 12 were tested for the resistance to hydrolysis under different hydrolyzing conditions with respect to the reagent, temperature and time, with the results as shown in Table 4.

Additional experiments were conducted as in Example 10 so as to produce isocholesteryl stearate (Control 4) and isocholesteryl oleate (Control 5). These conventional esters as well as cholesteryl stearate (Control 1) and cholesteryl oleate (Control 3) were also tested for the resistance to hydrolysis for the purpose of comparison. Table 4 also shows the results for the control cases.

TABLE 4

| | Hydrolyzing Conditions Rate of Hydrolysis (%) | | | | | |
|---|---|---|---|---|---|---|
| | ½N alcoholic coustic potash (25 ml) 85° C. | 1N alcoholic coustic potash (20 ml) 85° C. | | 1N n-propyl-alcohol solution of KOH (20 ml) 130 ~ 145° C. | | |
| Ester | 2 hrs. | 2 hrs. | 4 hrs. | 1 hr. | 2 hrs. | 4 hrs. |
| Example 8 | 7 | 9 | 9 | 17 | 21 | 32 |
| Example 9 | 8 | 11 | 12 | 22 | 39 | 48 |
| Example 10 | 6 | 7 | 7 | 15 | 26 | 36 |
| Example 11 | 3 | 4 | 4 | 8 | 11 | 13 |
| Example 12 | 7 | 9 | 9 | 16 | 19 | 29 |
| Control 1 | 100 | 100 | 100 | 100 | 100 | 100 |
| Control 4 | 78 | 85 | 87 | 88 | 93 | 95 |
| Control 3 | 100 | 100 | 100 | 100 | 100 | 100 |
| Control 5 | 81 | 86 | 90 | 93 | 95 | 96 |

Table 4 shows that the isocholesterol ester is superior to the cholesterol ester in resistance to hydrolysis. Particularly, the isocholesterol ester of the present invention is excellent in resistance to hydrolysis.

The esters of Examples 8 to 12, Controls 4 and 5, and lanolin were tested for the water-embracing property as in Table 3, with the results as shown in Table 5.

TABLE 5

| | Water-Embracing Property | | | |
|---|---|---|---|---|
| | Ester | Ester Addition to Vaseline | | |
| Ester | itself | 2% | 4% | 6% |
| Example 8 | 200 g | 80 g | 100 g | 90 g |
| Example 9 | 160 g | 65 g | 90 g | 85 g |
| Example 10 | 190 g | 80 g | 95 g | 90 g |
| Example 11 | 220 g | 95 g | 110 g | 100 g |
| Example 12 | 210 g | 90 g | 105 g | 95 g |
| Control 4 | 70 g | 25 g | 45 g | 40 g |
| Control 5 | 85 g | 23 g | 44 g | 38 g |
| Lanolin | 60 g | 15 g | 30 g | 25 g |

Table 5 shows that the ester of the present invention is superior to the linear carboxylic acid ester and lanolin in water-embracing property.

The esters of Examples 8 to 12 were also tested for the irritativeness to the human skin. Specifically, a closed patch test was performed as follows: A lint cloth one inch square was coated with the ester sample and attached to the skin area of a healthy person on the flexion side of the upper arm from which the horny layer and sebum have been removed. The lint cloth thus attached to the skin area was covered with an oilpaper and the oilpaper was fixed to the skin at four corners by a sticking plaster, followed by bandaging the ester-applied portion. This condition was maintained for 24 hours, 48 hours and 72 hours. This test was applied to 10 healthy men and 10 healthy women. Irritativeness was not recognized at all in any of Examples 8 to 12.

EXAMPLE 13

An esterification reaction was carried out at 220° to 230° C. under reflux of xylene between 43.3 g (0.30 mole) of 2-ethylhexanoic acid and 63.9 g (0.15 mole) of lanosterol in the presence of 0.32 g, which is 0.3% of the reactants, of p-toluenesulfonic acid. The reaction was continued until water was generated in an amount substantially equal to the calculation value. After the reaction, xylene was removed from the reaction mixture, followed by further removing the unreacted 2-ethylhexanoic acid at 180° to 200° C. under a reduced pressure so as to obtain 84.0 g of the desired ester of yellowish brown transparent liquid form. The product ester was found to exhibit an acid value of 0.1 and a hydroxyl value of 3.5.

EXAMPLE 14

An esterification reaction was carried out at 220° to 250° C. under reflux of xylene between 28.7 g (0.10 mole) of Diadole 18GA and 34.2 g (0.08mole) of dihydrolanosterol in the presence of 0.3 g, which is 0.5% of the reactants, of tin chloride catalyst. The reaction was continued until water was generated in an amount substantially equal to the calculation value. After the reaction, the catalyst was removed from the reaction mixture by means of filtration, followed by further removing the unreacted acid at 180° to 250° C. under a reduced pressure so as to obtain 45.6 g of the desired ester of yellow transparent liquid form. The product ester was found to exhibit an acid value of 0.2 and a hydroxyl value of 5.3.

As apparent from the above Examples, the steroid esters of the present invention are excellent in resistance to hydrolysis, exhibit a high water-embracing property and do not irritate the human skin. Thus, these esters can be used effectively as an oil phase material, base material or emulsifying additive of cosmetics and ointments. The cosmetics mentioned include, for example, creamy cosmetics for the skin such as cold cream, nutritive cream and cleansing cream; stick cosmetics for the skin such as lipstick and eyeshadow; pasty cosmetics for the hair such as pomade; and liquid or emulsified cosmetics for the hair such as hair dresser and hair rinse. These cosmetics may contain the other oil phase material of ordinary cosmetics such as liquid paraffin, squalene, olive oil, castor oil and ester oil and/or the wax used in the ordinary cosmetics such as candelilla wax, beeswax, lanolin, vaseline and paraffin in addition to the steroid ester of the present invention. Further, the cosmetics containing the steroid ester of the present invention may also contain various additives such as surfactant, wetting agent, pigment, perfume, antioxidant and detergent, e.g., borax. It is also possible to add, for example, water to the cosmetics.

The steroid ester of the present invention is also suitable for use as the base material of ointments, as mentioned above. The ointment mentioned may contain the other oil phase material, wax, additives, water, etc. mentioned above in conjunction with the cosmetics, in addition to the steroid ester of the present invention. It is also possible to add a medically active component to the ointment.

The composition providing the cosmetics and ointments mentioned above generally contains 0.05 to 50%, preferably 0.1 to 10% of the steroid ester of the present invention.

Described in the following are Examples of the cosmetics and ointment base materials of the present invention.

EXAMPLE A

An oil phase containing 50% by weight of liquid paraffin, 15% by weight of beeswax and 5.0% by weight of the ester of Example 5 was heated to 80° C. for uniformly dispersing the components, followed by slowly adding to the oil phase an aqueous phase containing 0.8% by weight of borax, said aqueous phase being heated to 80° C., while stirring the system. Then, the system was cooled to 55° C. and a proper amount of perfume was added thereto, followed by further cooling the system to 35° C. so as to obtain a cold cream.

EXAMPLE B

An oil phase containing 10.0% by weight of stearic acid, 2.0% by weight of the ester of Example 3, 2.0% by weight of the ester of Example 6, 8.0% by weight of olive oil and a proper amount of tocopherol (antioxidant) was heated to 80° C. for uniformly dispersing the components, followed by slowly adding to the oil phase an aqueous phase containing 6.0% by weight of sodium laurylimino dipropionate, said aqueous phase being heated to 75° C. The system was fully stirred and cooled to 35° C. so as to obtain a nutritive cream.

EXAMPLE C

A cleansing cream was produced by using an oil phase of the following composition and an aqueous phase of the following composition:

|  | % by weight |
|---|---|
| Oil Phase |  |
| Liquid paraffin | 53.0 |
| White vaseline | 10.0 |
| Ester of Example 7 | 3.0 |
| Polyoxyethylene(4) glyceryl ester distearate | 1.5 |
| Polyoxyethylene(3) stearyl ether | 3.0 |
| Polyoxyethylene(10) oleyl ether | 2.0 |
| Polyoxyethylene(25) octyl ether | 1.0 |
| Aqueous Phase |  |
| Polyethyleneglycol 800 | 0.5 |
| Sodiumlaurylsulfate | 0.2 |
| Glycerin | 0.1 |
| Water | 25.7 |

Specifically, the oil phase was heated to 75° C. for uniformly dispersing the components, followed by slowly adding the aqueous phase heated to 70° C. to the oil phase. The system was fully stirred and cooled to 30° C. so as to obtain the desired cleansing cream.

EXAMPLE D

A hair dresser was produced by using an oil phase of the following composition and an aqueous phase of the following composition:

|  | % by weight |
|---|---|
| Oil Phase |  |
| Liquid paraffin | 23.0 |
| Ester of Example 4 | 1.0 |
| Cosmole 525 (trademark of neopentyl glycol-di-2-ethylhexanate produced by Nisshin Seiyu K.K.) | 2.0 |
| Polyoxyethylene(10) glyceryl tristearate | 4.0 |
| Polyoxyethylene(12) stearyl ether stearate | 0.7 |
| Polyoxyethylene(8) oleyl ether | 0.4 |
| Polyoxyethylene(10) lauryl ether | 0.2 |
| Polyoxyethylene(10) butyl ether | 0.1 |
| Aqueous Phase |  |
| Polyethyleneglycol 300 | 0.05 |
| Propyleneglycol | 0.03 |
| Water | 68.52 |

Specifically, the oil phase was heated to 70° C. for uniformly dispersing the components, followed by adding the aqueous phase heated to 65° C. to the oil phase. The system was fully stirred and cooled to 30° C. so as to obtain the desired hair dresser.

EXAMPLE E

A pomade was produced by using an oil phase of the following composition, an aqueous phase containing 5.0% by weight of glycerin, and a proper amount of perfume:

| Oil Phase | % by weight |
|---|---|
| Castor oil | 2.0 |
| Cured castor oil | 2.0 |
| Ester of Example 6 | 2.0 |
| Polyoxyethylene(12) cured castor oil monolaurate | 10.0 |
| Polyoxyethylene(15) cured castor oil monostearate | 18.0 |
| Polyoxyethylene(45) stearyl ether | 15.0 |

Specifically, the oil phase was heated to 80° C. and the perfume was added thereto, followed by slowly adding the aqueous phase heated to 80° C. to the oil phase. The system was fully stirred and cooled to 60° C., followed by standing still the system. After completion of defoaming, the system was further cooled so as to obtain the desired pomade.

EXAMPLE F

A hair rinse of emulsion form was produced by using an oil phase of the following composition and an aqueous phase of the following composition:

|  | % by weight |
|---|---|
| Oil Phase |  |
| Cetanol | 1.5 |
| Ester of Example 5 | 0.5 |
| Stearyldimethylbenzene ammonium chloride | 2.0 |
| Glycerylmonostearate | 5.0 |
| Aqueous Phase |  |
| Propyleneglycol | 4.0 |
| Water | 87.0 |

Specifically, the oil phase was heated to 70° C. for uniformly dispersing the components, followed by slowly adding the aqueous phase heated to 75° C. to the oil phase. The system was gently stirred so as not to generate foams and cooled to 30° C., thereby obtaining the desired hair rinse.

EXAMPLE G

A lipstick was produced by using a base material of the following composition, a coloring matter consisting of 2.0% by weight of titanium oxide and 0.5% by weight of a red-type colorant, and 1.0% by weight of perfume:

| Base Material | % by weight |
|---|---|
| Castor oil | 50.0 |
| Palmityl alcohol | 10.0 |
| Beeswax | 10.0 |
| Ceresin | 10.0 |
| Liquid paraffin | 5.5 |
| Candelilla wax | 5.0 |
| Ester of Example 3 | 4.0 |
| Carnauba wax | 2.0 |

Specifically, the base material was heated to 80° C. for uniformly dispersing the components. Then, the coloring matter was added to the base material and the resultant mixture was uniformly kneaded by a roll mill. Further, the perfume was added to the kneaded mass. After defoaming, the system was poured into a mold, followed by rapidly cooling the mold so as to obtain the desired lipstick.

EXAMPLE H

An ointment base material was produced by using an oil phase of the following composition and an aqueous phase of the following composition:

|  | % by weight |
|---|---|
| Oil Phase | |
| Liquid paraffin | 20.0 |
| White vaseline | 10.0 |
| Cetanol | 20.0 |
| Ester of Example 4 | 4.0 |
| Polyoxyethylene(15) stearyl ether | 4.0 |
| Aqueous Phase | |
| Sodiumlaurylsulfate | 1.0 |
| Water | 41.0 |

Specifically, the oil phase was heated to 70° C. for uniformly dispersing the components, followed by adding the aqueous phase heated to 70° C. to the oil phase so as to emulsify the system. The emulsion thus prepared was cooled so as to obtain the desired base material of ointment.

EXAMPLE I

A lipstick was produced by using an oil phase of the following composition, a coloring matter consisting of 2.0% by weight of titanium oxide and 6.0% by weight of red colorant, and a proper amount of perfume:

| Oil Phase | % by weight |
|---|---|
| Castor oil | 45.0 |
| Ester of Example 5 | 29.0 |
| Beeswax | 5.0 |
| Ceresin | 4.0 |
| Candelilla wax | 7.0 |
| Carnauba wax | 2.0 |
| Antioxidant, Corrosion inhibitor | proper amount |

Specifically, the oil phase was heated for melting and uniformly dispersing the components, followed by adding the coloring matter to the oil phase and uniformly kneading the mixture by a roll mill. Then, the kneaded mixture was melted again and the perfume was added thereto. After defoaming, the system was poured into a mold and, then, rapidly cooled so as to solidify the system. Finally, the molding was released from the mold and put in a container so as to obtain the desired lipstick.

EXAMPLE J

An oil phase containing 35.0% by weight of liquid paraffin, 15.0% by weight of vaseline, 14.0% by weight of beeswax and 6.0% by weight of the ester of Example 8 was heated to 80° C. for uniformly dispersing the components, followed by slowly adding an aqueous phase containing 0.8% by weight of borax, said aqueous phase being heated to 80° C., to the oil phase, while stirring the system. Then, the system was cooled to 35° C. so as to obtain a cold cream.

EXAMPLE K

An oil phase containing 10.0% by weight of stearic acid, 5.0% by weight of the ester of Example 9, 8.0% by weight of olive oil, and a proper amount of an antioxidant was heated to 80° C. for uniformly dispersing the components, followed by slowly adding an aqueous phase containing 6.0% by weight of sodiumlaurylimino dipropionate, said aqueous phase being heated to 80° C., to the oil phase. The system was cooled to 35° C. so as to obtain a nutritive cream.

EXAMPLE L

A cleansing cream was produced by using an oil phase of the following composition and an aqueous phase of the following composition:

|  | % by weight |
|---|---|
| Oil Phase | |
| Liquid paraffin | 62.0 |
| Ester of Example 10 | 4.0 |
| Polyoxyethylene(4) glyceryl ether distearate | 0.5 |
| Polyoxyethylene(3) stearyl ether | 1.0 |
| Polyoxyethylene(10) oleyl ether | 0.5 |
| Polyoxyethylene(25) octyl ether | 0.5 |
| Aqueous Phase | |
| Polyethyleneglycol 800 | 0.2 |
| Sodiumlaurylsulfate | 0.1 |
| Glycerin | 0.1 |
| Water | balance |

Specifically, the oil phase was heated to 75° C. for uniformly dispersing the components, followed by slowly adding the aqueous phase heated to 70° C. to the oil phase while stirring the system. Then, the system was cooled to 30° C. so as to obtain the desired cleansing cream.

EXAMPLE M

A lipstick was produced by using a base material of the following composition, a coloring matter of the following composition, and a proper amount of perfume:

|  | % by weight |
|---|---|
| Base Material | |
| Castor oil | 50.0 |
| Cetanol | 10.0 |
| Beeswax | 10.0 |
| Ceresin | 10.0 |
| Liquid paraffin | 5.5 |
| Candelilla wax | 5.0 |
| Ester of Example 11 | 4.0 |
| Carnauba wax | 2.0 |
| Coloring Matter | |
| Titanium oxide | 2.0 |
| Red colorant | 0.5 |

Specifically, the base material was heated to 80° C. for uniformly dispersing the components, followed by adding the coloring matter to the base material and sufficiently kneading the mixture by a roll mill. The kneaded mixture was heated and the perfume was added thereto, followed by standing still the system so as to defoam the system. Finally, the system was rapidly cooled so as to obtain the desired lipstick.

EXAMPLE N

An oil phase containing 1.5% by weight of cetanol, 0.5% by weight of the ester of Example 2, 0.5% by weight of stearyldimethylbenzylammonium chloride and 3.0% by weight of glycerylmonostearate was heated to 70° C. for uniformly dispersing the components, followed by slowly adding to the oil phase an aqueous phase containing 4.0% by weight of propyleneglycol, said aqueous phase being heated to 70° C., while stirring the system. Then, the system was cooled to 30° C. so as to obtain a hair rinse.

EXAMPLE O

A base material of ointment was produced by using an oil phase of the following composition and an aqueous phase containing 0.2% by weight of sodiumlaurylsulfate:

| Oil Phase | % by weight |
|---|---|
| Liquid paraffin | 20 |
| White vaseline | 10 |
| Cetanol | 20 |
| Ester of Example 8 | 4 |
| Polyoxyethylene(15) stearyl ether | 1 |

Specifically, the oil phase was heated to 70° C. for uniformly dispersing the components, followed by adding the aqueous phase heated to 70° C. to the oil phase so as to emulsify the system. The emulsion was then cooled so as to obtain the desired base material of ointment.

EXAMPLE P

A lipstick was produced as in Example I by using an oil phase of the following composition, a coloring matter of the following composition, and a proper amount of perfume:

| | % by weight |
|---|---|
| Oil Phase | |
| Castor oil | 50.0 |
| Ester of Example 8 | 24.0 |
| Beeswax | 5.0 |
| Ceresin | 4.0 |
| Candelilla wax | 7.0 |
| Carnauba wax | 2.0 |
| Antioxidant, Corrosion inhibitor | proper amount |
| Coloring Matter | |
| Titanium oxide | 2.0 |
| Red colorant | 6.0 |

What we claim is:

1. A cosmetic comprising a cosmetic ingredient and a steroid ester obtained by reacting at least one steroid component which is a trimethylsteroid or a mixture comprising said trimethylsteroid, and wherein the trimethylsteroid is dihydrolanosterol, lanosterol, dihydroagnosterol, agnosterol, cycloartanol, cycloartenol, 2,4-methylenecyloartanol, cyclolaudenol, cyclobranol, isocholesterol or a mixture thereof, with at least one carboxylic acid-based component selected from the group consisting of free α-branched carboxylic acids having a general formula $$R^1-\underset{R^2}{\underset{|}{CH}}-COOH$$

(where $R^1$ is an alkyl group having at least two carbon atoms, and $R^2$ is an alkyl group having at least four carbon atoms) and reactive derivatives of said α-branched carboxylic acid which are acid halides or anhydrides, said cosmetic is a creamy cosmetic for the skin including a cold cream, a nutritive cream, and a cleansing cream, a stick cosmetic for the skin including a lipstick and an eyeshadow, a pasty cosmetic for the hair including a pomade, or a liquefied or emulsified cosmetic for the hair including a hair dresser and a hair rinse.

2. The cosmetic according to claim 1, wherein the total number of carbon atoms contained in $R^1$ and $R^2$ is at most 24.

3. The cosmetic according to claim 2, wherein the carboxylic acid-based component is the free acid.

4. The cosmetic according to claim 3, wherein the free acid is selected from the group consisting of 2-ethylhexanoic acid, 2-hexyldecanoic acid, 2-heptylundecanoic acid, acid of the chemical structure:

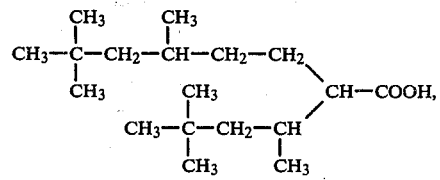

2-decyltetradecanoic acid, 2-undecyltetradecanoic acid, 2-decylpentadecanoic acid, 2-undecylpentadecanoic acid and a mixture thereof.

5. The cosmetic according to claim 2, wherein the carboxylic acid-based component is the reactive derivative.

6. The cosmetic according to claim 5, wherein the reactive derivative is an acid chloride.

7. The cosmetic according to claim 6, wherein the acid chloride is selected from the group consisting of 2-ethylhexanoic acid chloride, 2-hexyldecanoic acid chloride, 2-heptylundecanoic acid chloride, chloride of acid of the chemical structure:

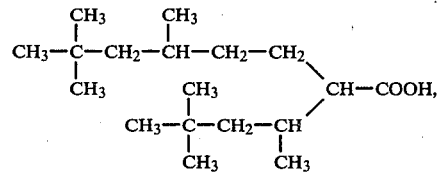

2-decyltetradecanoic acid chloride, 2-undecyltetradecanoic acid chloride, 2-decylpentadecanoic acid chloride, and a mixture thereof.

8. The cosmetic according to any one of claims 1 to 7, further comprising a second steroid component which is cholesterol.

9. The cosmetic according to claim 8, wherein the steroid ester is liquid under room temperature.

10. The cosmetic according to claim 8, wherein the rate of hydrolysis of the steroid ester brought about by ½ N alcoholic caustic potash is less than 20%.

11. The cosmetic according to claim 8, wherein the steroid ester exhibits a water-embracing property enough to permit forming a w/o type emulsion together with water in an amount at least two times as much in weight as the ester.

12. The cosmetic according to any one of claims 1 to 7, wherein the steroid ester is liquid under room temperature.

13. The cosmetic according to any one of claims 1 to 7, wherein the rate of hydrolysis of the steroid ester brought about by ½ N alcoholic caustic potsh is less than 15%.

14. The cosmetic according to any one of claims 1 to 7, wherein the steroid ester exhibits a water-embracing property enough to permit forming a w/o type emulsion together with water in an amount at least 1.5 times as much in weight as the ester.

15. An ointment comprising an ointment ingredient and a steroid ester obtained by reacting at least one steroid component which is a trimethylsteroid or a mixture comprising said trimethylsteroid, and wherein the trimethylsteroid is dihydrolanosterol, lanosterol, dihydroagnosterol, agnosterol, cycloartanol, cycloartenol, 2,4-methylenecycloartanol, cyclolaudenol, cyclobranol, isocholesterol or a mixture thereof, with at least one carboxylic acid-based component selected from the group consisting of free α-branched carboxylic acids having a general formula

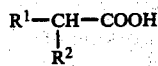

(where $R^1$ is an alkyl group having at least two carbon atoms, and $R^2$ is an alkyl group having at least four carbon atoms) and reactive derivatives of said α-branched carboxylic acid which are acid halides or anhydrides 16. The ointment according to claim 15, wherein the total number of carbon atoms contained in $R^1$ and $R^2$ is at most 24.

17. The ointment according to claim 16, wherein the carboxylic acid-based component is the free acid.

18. The ointment according to claim 17, wherein the free acid is selected from the group consisting of 2-ethylhexanoic acid, 2-hexyldecanoic acid, 2-heptylundecanoic acid, acid of the chemical structure:

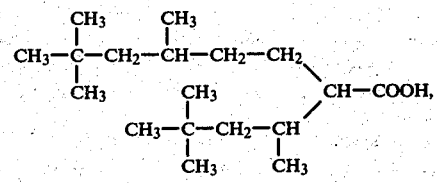

2-decyltetradecanoic acid, 2-undecyltetradecanoic acid, 2-decylpentadecanoic acid, 2-undecylpentadecanoic acid, and a mixture thereof.

19. The ointment according to claim 15, wherein the carboxylic acid-based component is the reactive derivative.

20. The ointment according to claim 19, wherein the reactive derivative is an acid chloride.

21. The ointment according to claim 20, wherein the acid chloride is selected from the group consisting of 2-ethylhexanoic acid chloride, 2-hexyldecanoic acid chloride, 2-heptylundecanoic acid chloride, chloride of acid of the chemical structure:

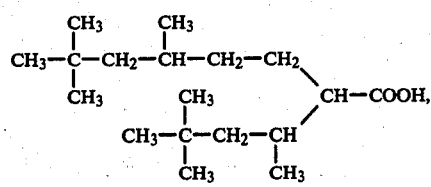

2-decyltetradecanoic acid chloride, 2-undecyltetradecanoic acid chloride, 2-decylpentadecanoic acid chloride, 2-undecylpentadecanoic acid chloride, and a mixture thereof.

22. The ointment according to any one of claims 15 to 21, further comprising a second steroid component which is cholesterol.

23. The ointment according to claim 22, wherein the steroid ester is liquid under room temperature.

24. The ointment according to claim 22, wherein the rate of hydrolysis of the steroid ester brought about by ½ N alcoholic caustic potash is less than 20%.

25. The ointment according to claim 22, wherein the steroid ester exhibits a water-embracing property enough to permit forming a w/o type emulsion together with water in an amount at least two times as much in weight as the ester.

26. The cosmetic according to any one of claims 15 to 21, wherein the steroid ester is liquid under room temperature.

27. The cosmetic according to any one of claims 15 to 21, wherein the rate of hydrolysis of the steroid ester brought about by ½ N alcoholic caustic potash is less than 15%.

28. The cosmetic according to any one of claims 15 to 21, wherein the steroid ester exhibts a water-embracing property enough to permit forming a w/o type emulsion together with water in an amount at least 1.5 times as much as in weight as the ester.

29. The cosmetic of claim 1 which is a cold cream, nutritive cream, cleansing cream, lipstick, hair pomade, hair dresser or a hair rinse and the steroid ester is present in an amount of from 0.05 to 50%.

30. The ointment of claim 15 wherein the steroid ester is present in an amount of from 0.05 to 50%.

31. The cosmetic of claim 1, 15, 32, or 42, wherein said cosmetic ingredient is a cosmetic oil, wax, surfactant, wetting agent, pigment, perfume, antioxidant, detergent or mixtures thereof.

32. A cosmetic comprising a cosmetic ingredient and a steroid ester obtained by reacting at least one steroid component which is cholesterol with at least one carboxylic acid-based component selected from the group consisting of free α-branched carboxylic acids having a general formula

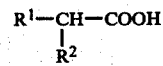

(where $R^1$ is an alkyl group having at least two carbon atoms, and $R^2$ is an alkyl group having at least four carbon atoms) and reactive derivatives of said α-branched carboxylic acid which are acid halides or anhydrides, said cosmetic is a creamy cosmetic for the skin including a cold cream, a nutritive cream, and a cleansing cream, a stick cosmetic for the skin including a lipstick and an eyeshadow, a pasty cosmetic for the hair including a pomade, or a liquefied or emulsified cosmetic for the hair including a hair dresser and a hair rinse.

33. The cosmetic according to claim 32, wherein the total number of carbon atoms contained in $R^1$ and $R^2$ is at most 24.

34. The cosmetic according to claim 33, wherein the carboxylic acid-based component is the free acid.

35. The cosmetic according to claim 34, wherein the free acid is selected from the group consisting of 2-ethylhexanoic acid, 2-hexyldecanoic acid, 2-heptylundecanoic acid, an acid of the chemical structure:

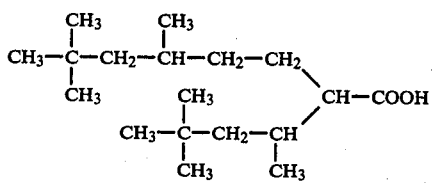

2-decyltetradecanoic acid, 2-undecyltetradecanoic acid, 2-decylpentadecanoic acid, 2-undecylpentadecanoic acid, and mixtures thereof.

36. The cosmetic according to claim 33, wherein the carboxylic acid-based component is the reactive derivative.

37. The cosmetic according to claim 36, wherein the reactive derivative is an acid chloride.

38. The cosmetic according to claimm 37, wherein the acid chloride is selected from the group consisting of 2-ethylhexanoic acid chloride, 2-hexyldecanoic acid chloride, 2-heptylundecanoic acid chloride, a chloride of an acid of the chemical structure:

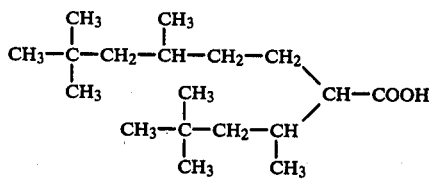

2-decyltetradecanoic acid chloride, 2-undecyltetradecanoic acid chloride, 2-decylpentadecanoic acid chloride, and mixtures thereof.

39. The cosmetic according to any one of claims 32 to 38, wherein the steroid ester is liquid under room temperature.

40. The cosmetic according to any one of claims 32 to 38, wherein the rate of hydrolysis of the steroid ester brought about by ½ N alcoholic caustic potash is less than 15%.

41. The cosmetic according to any one of claims 32 to 38, wherein the steroid ester exhibits a water-embracing property enough to permit forming a w/o type emulsion together with water in an amount at least 1.5 times as much in weight as the ester.

42. An ointment comprising an ointment ingredient and a steroid ester obtained by reacting at least one steroid component which is cholesterol with at least one carboxylic acid-based component selected from the group consisting of free α-branched carboxylic acids having a general formula

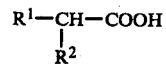

(where $R^1$ is an alkyl group having at least two carbon atoms, and $R^2$ is an alkyl group having at least four carbon atoms) and reactive derivatives of said α-branched carboxylic acid which are acid halides or anhydrides 43. The ointment according to claim 42, wherein the total number of carbon atoms contained in $R^1$ and $R^2$ is at most 24.

44. The ointment according to claim 43, wherein the carboxylic acid-based component is the free acid.

45. The ointment according to claim 44, wherein the free acid is selected from the group consisting of 2-ethylhexanoic acid, 2-hexyldecanoic acid, 2-heptylundecanoic acid, an acid of the chemical structure:

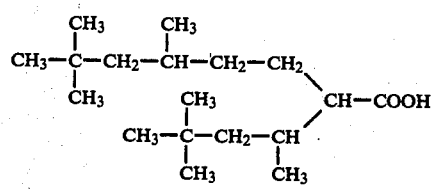

2-decyltetradecanoic acid, 2-undecyltetradecanoic acid, 2-decylpentadecanoic acid, 2-undecylpentadecanoic acid, and mixtures thereof.

46. The ointment according to claim 42, wherein the carboxylic acid-based component is the reactive derivative.

47. The ointment according to claim 46, wherein the reactive derivative is an acid chloride.

48. The ointment according to claim 47, wherein the acid chloride is selected from the group consisting of 2-ethylhexanoic acid chloride, 2-hexyldecanoic acid chloride, 2-heptylundecanoic acid chloride, a chloride of an acid of the chemical structure:

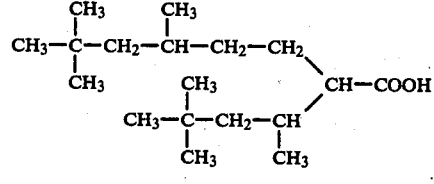

2-decyltetradecanoic acid chloride, 2-undecyltetradecanoic acid chloride, 2-decylpentadecanoic acid chloride, 2-undecylpentadecanoic acid chloride, and mixtures thereof.

49. The ointment according to any one of claims 43 to 48, wherein the steroid ester is liquid under room temperature.

50. The ointment according to any one of claims 43 to 48, wherein the rate of hydrolysis of the steroid ester brought about by ½ N alcoholic caustic potash is less than 15%.

51. The ointment according to any one of claims 43 to 48, wherein the steroid ester exhibits a water-embracing property enough to permit forming a w/o type emulsion together with water in an amount at least 1.5 times as much in weight as the ester.

* * * * *